US006336908B1

(12) United States Patent
Slautterback

(10) Patent No.: US 6,336,908 B1
(45) Date of Patent: Jan. 8, 2002

(54) DETACHABLE BACK SUPPORT, APRON AND METHOD

(76) Inventor: Ernest Gerald Slautterback, 1880 Merion La., Coral Springs, FL (US) 33071

( * ) Notice: Subject to any disclaimer, the term of this patent is extended or adjusted under 35 U.S.C. 154(b) by 0 days.

(21) Appl. No.: 09/495,579

(22) Filed: Feb. 1, 2000

(51) Int. Cl.[7] ............................... A61F 5/00; A41F 9/00
(52) U.S. Cl. ............................................. 602/19; 2/312
(58) Field of Search .................... 602/5, 19, 60–61; 2/311–312, 44, 45, 338; 128/95.1, 96.1, 99.1, 100.1, 101.1, 846, 869, 876, 845

(56) References Cited

U.S. PATENT DOCUMENTS

| | | | |
|---|---|---|---|
| 5,318,507 A | | 6/1974 | Greengarg |
| 5,040,524 A | * | 8/1991 | Votel et al. .................... 602/19 |
| 5,147,261 A | | 9/1992 | Smith et al. |
| 5,148,549 A | * | 9/1992 | Sydor ................................ 2/1 |
| 5,257,419 A | * | 11/1993 | Alexander ........................ 2/44 |
| 5,388,274 A | * | 2/1995 | Gloven et al. .................. 2/338 |
| 5,413,262 A | * | 5/1995 | Dewire et al. .............. 224/675 |
| 5,548,843 A | * | 8/1996 | Chase et al. ................... 2/102 |
| 5,656,020 A | | 8/1997 | Greengarg |
| 5,656,021 A | | 8/1997 | Greengarg |
| 5,693,006 A | | 12/1997 | Slautterback |
| 5,967,145 A | * | 10/1999 | Knapik et al. .............. 128/869 |

* cited by examiner

Primary Examiner—Denise Pothier

(57) ABSTRACT

A back support comprising a back support belt having flaps with fastening material for releaseably securing the flap ends in overlying relationship. Side pulls extend from the back portion of the support belt and also are provided with fastening material for securing the ends of the side pulls to the support belt and to each other. The side pulls are formed of overlying inner and outer portions in a known manner. The support belt has mounted thereon quick lock release buckles for attaching to the back support accessories, such as a standard apron having waist ties. The quick lock release buckles have male and female halves and pass through type securements on the separable halves. Preferably one of the securements is a double pass through type on the male halves in order to provide adjustability in securing the waist ties of a standard apron. Another feature of the invention is the provision of a means for holding the side pulls adjacent the secured flaps when the back support belt is mounted on a wearer. To this end vertical strips are provided on the outside surface of the flaps between the positions where the side pulls are secured to the belt and their ends. These strips pass between the overlying elements of the side pulls.

7 Claims, 2 Drawing Sheets

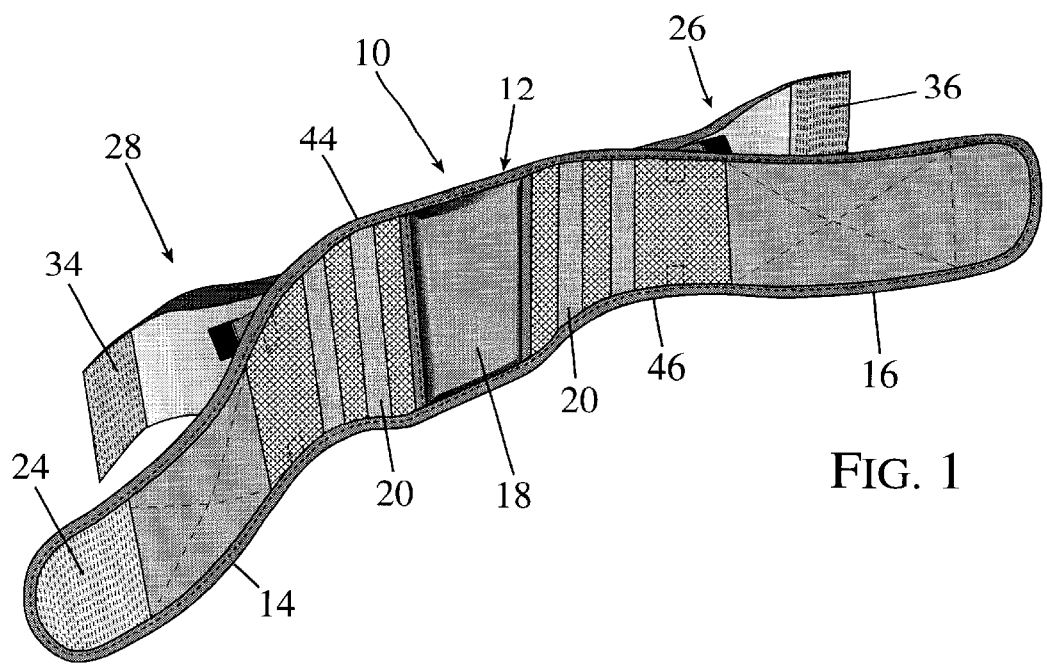
FIG. 1
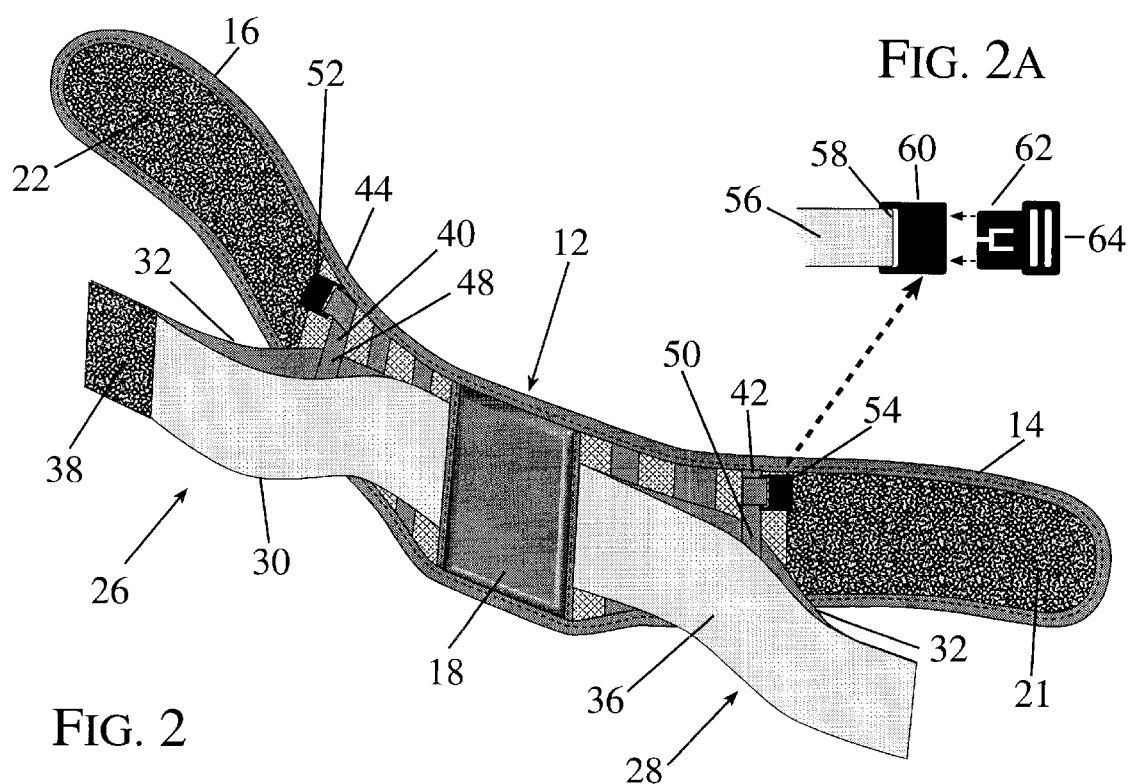
FIG. 2
FIG. 2A

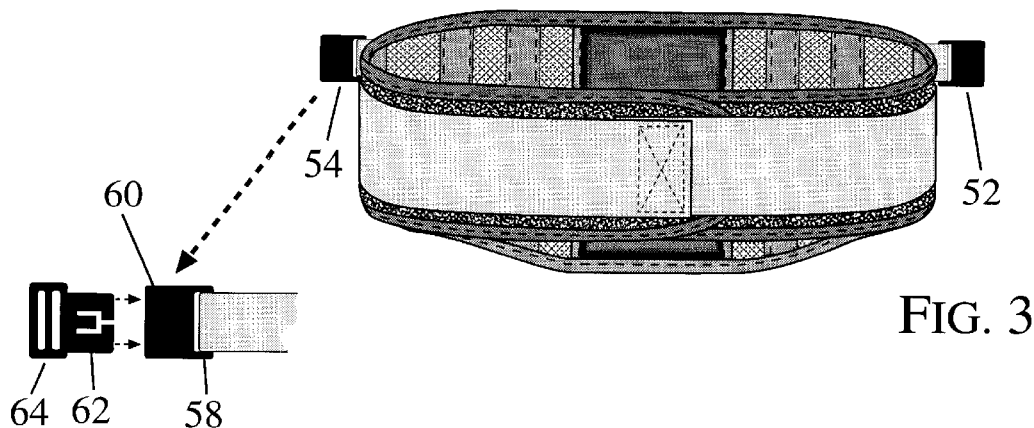
FIG. 3
FIG. 3A
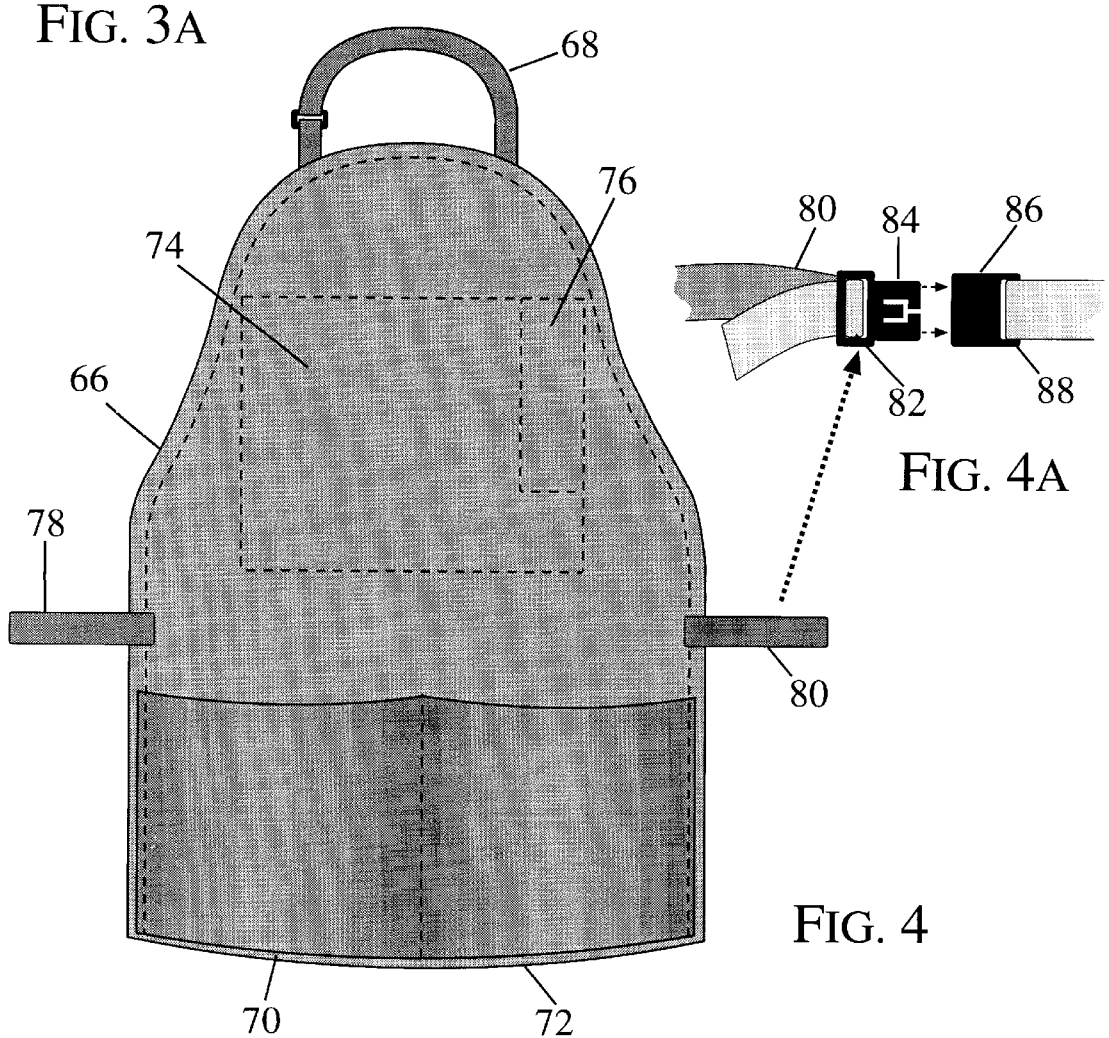
FIG. 4
FIG. 4A

DETACHABLE BACK SUPPORT, APRON AND METHOD

The present invention relates to back supports or lifting belts, and more particularly to a quick release mode of attaching aprons or other accessories to such supports.

SUMMARY OF THE PRIOR ART

Individuals who wear back supports may also wear an apron at the same time. The apron is commonly worn over the back support, but may also be worn under the back support. Either way can be cumbersome, as each device is independent of the other. Commercial back supports with integrated aprons are also available. However, most employers would prefer to utilize the same apron design for all employees, regardless of whether or not they wear a back support. There is thus an outstanding need for a back support which is capable of being combined with a quickly attachable and detachable apron, wherein the apron is usable both with and without a back support.

At the current time there exists a wide variety of back supports and lifting belts, many of which have removably attached accessories, such as aprons. Examples of such types of devices are those shown, by way of example, in the following U.S. Patents: U.S. Pat. No. 5,147,261, issued to Neil Smith, et al. Sep. 15, 1992; U.S. Pat. No. 5,693,006, issued to Ernest Gerald Slautterback Dec. 2, 1997; U.S. Pat. No. 5,656,021, issued to Gerson M. Greengarg Aug. 12, 1997; U.S. Pat. No. 5,656,020 issued to Gerson M. Greengarg Aug. 12, 1997; and U.S. Pat. No. 5,318,507 issued to Gerson M. Greengarg Jun. 7, 1994.

U.S. Pat. No. 5,147,261 is directed to what has become a basic lifting belt. The patent describes the belt as a combination of two belts, a lumbar belt, and an abdominal belt. The lumbar belt is the inner belt and has a lumbar compression pad in its mid-rear portion. Two flaps extend from the compression pad and are releasably secured together at their ends by a hook and loop type connection. The lumbar belt has attached to its outer surface a pair of side pulls, which use loop and hook connections to secure the side pulls to the outside of the lumbar belt, and to secure the ends of the side pulls to one another.

U.S. Pat. Nos. 5,318,507, 5,656,020, and 5,656,021 describe basically the same types of devices. Those patents illustrate and describe various combinations of a detachable back belt, an apron, and a lifting belt. The lifting belt is a body engaging member With ends that are closed underneath the apron. The patents describe methods for applying the combination of apron, lifting belt, suspenders, and detachable back belt to the user. In one method the lifting belt is first placed around the user. Thereafter, the apron is secured to the overlapped outer ends of the lifting belt, and the suspenders are secured over the shoulders and to the apron. Subsequently the detachable back belt is secured to the lifting belt and to the apron. In another method the combination of apron, lifting belt, suspenders, and detachable back belt are applied to the user by first putting on the apron. Thereafter, the lifting belt is slipped under the apron, the suspenders secured over the shoulders, and the suspenders optionally adjusted for short chested or long torso persons.

U.S. Pat. No. 5,693,006 describes an assessory base for use with lifting belts. The lifting belts are of the basic type described in U.S. Pat. No. 5,147,261, described earlier herein. The side pulls and the flaps are utilized for a sandwiching type securement of the assessory base between the side pulls and the belt flaps.

SUMMARY OF THE INVENTION

The present invention is directed to a back support with sewn in quick lock release buckles for attaching accessories, such as aprons. The quick lock release buckles have male halves which are provided with double feed through securements, and female halves which have single feed through securements. The single feed throughs are used to attach the female halves of the buckles to the back support. The double feed throughs are used to attach the waist ties of an apron to the back support. The waist ties may be of varying width of up to approximately one inch. Each waist tie is threaded through the double feed through securement of the male half of one of the buckles. The single feed throughs of the female halves of the buckles are affixed to each side of the rear of the support belt. This affixation may use nylon webbing or similar material sewn to the support belt. To quickly attach the apron to the belt, the male and female halves of the quick lock release buckles are locked together. The apron waist ties are then adjusted to provide a proper fit of the apron. To remove the apron, the releases on the buckles are pressed and the buckle halves immediately part. The quick lock release buckles are available from numerous vendors. They may be utilized in the arrangement of the invention with either a center or a side release.

Another feature of the invention relates to the back support or belt having side pulls which are either sewn to the rear of the support base or belt, or affixed to the rear of the support base using hook and loop material. This aspect of the invention features a unique arrangement wherein the front or distal ends of the side pulls are held in close proximity to the support base or belt when they are not affixed thereto. On most back supports the fronts of the side pulls fall completely away from the support belt when they are not affixed. According to this feature of the invention the outside of the lumbar support belt includes a pair of vertical strips of nylon webbing. These vertical strips on the outside of the support belt are located at the sides of the belt, positioned between the affixed and distal ends of each of the side pulls. When the distal ends of the side pulls are not affixed, the vertical nylon webbing holds the side pulls close to the support base or belt. It does this by passing between the two portions of each of the side pulls, so that the inner portions of the side pulls are held snugly against the outer surface of the lumbar belt.

OBJECTS OF THE INVENTION

It is an object of the invention to provide a back support device having the capability of being efficiently and conveniently used with or without a standard apron.

It is a primary object of the invention to provide a back support device which includes a lumbar support belt with side pulls, wherein there is provision for quick attachment and detachment of an accessory, such as an apron.

It is another object of the invention to provide such quick attachment and detachment through the use of a novel arrangement of quick lock release buckles.

It is yet another object of the invention to fasten such quick release buckles between the lumbar support belt and the waist ties of an apron using nylon webbing fixed to support belt.

It is a still further object of the invention to provide a back support device having a lumbar support belt with side pulls wherein there is provision for preventing the side pulls from falling completely away from the lumbar support belt when the ends of the side pulls are unattached.

It is yet another object of the invention to provide such control of the position of the side pulls by nylon webbing or the like material mounted on the outside of the lumbar support belt in a novel fashion.

BRIEF DESCRIPTION OF THE DRAWINGS

Further objects and advantages of the invention will be better understood as the following description proceeds, taken in conjunction with the accompanying illustrative drawings, in which:

FIG. 1 is an exploded perspective view from the inside or wearer side of a typical back support belt, opened up to show the base or lumbar belt portion and the side pulls with the ends of the quick lock release buckles extending from the outside of the belt.

FIG. 2 is an exploded perspective view from the outside of the back support belt showing details of the side pulls and the mounting of the quick lock release buckles.

FIG. 2A is an exploded front view of a typical quick lock release buckle shown on the right in FIG. 2 used in the invention and shows the two halves of the buckle separated prior to locking together.

FIG. 3 is a front perspective view of a back support of the invention in a closed or wearing condition, showing the quick lock release buckles standing out from the sides of the support.

FIG. 3A is an exploded front view of one of the quick lock release buckles shown in FIG. 3 with the two halves of the buckle separated prior to locking together.

FIG. 4 shows a front elevation view of a typical apron with waist ties for use in the assemblage of the invention.

FIG. 4A is a perspective exploded view showing the separated halves of a quick lock release buckle with the male half of the buckle attached to a waist tie according to the invention.

DESCRIPTION OF A PREFERRED EMBODIMENT

Referring to FIG. 1, there is shown one preferred embodiment of a back support belt assembly 10 which comprises a lumbar belt 12 extending in two sections or flaps 14 and 16 from a lumbar compression pad 18. Vertical stays 20, which are preferably of spring steel, are provided on each side of the compression pad 18. The inner surfaces of the flaps 14 and 16 are preferably smooth for comfort of the wearer. Referring to FIGS. 1 and 2, the outer surfaces of the flaps 14 and 16, and the inner end surface of the flap 14, are respectively provided with hook and loop materials to releasably lock the flap ends to themselves. Preferably the outer surfaces are provided with loop material as shown at 21 and 22. This material extends from the ends of the flaps to adjacent the positions where the side pulls are held to the belt, as is presently explained in detail. The inner end surface of the other flap 14 is provided with hook material 24. The end of this flap 14 overlays the outer surface of the end of flap 16. For this reason the end of the flap 16 is sometimes referred to as the inner end, while the overlying end of flap 14 is referred to as the outer end. This hook and loop fastening provides adjustability to secure optimal fit to the body of the wearer. While the loop-hook relationship which is specifically described is desireable, reversal may be used along with equivalent removable securing members.

Referring to FIG. 2, the back support of the invention includes an abdominal belt comprised of side pulls 26 and 28 secured to the lumbar compression pad 18. In the specific embodiment of the invention illustrated in FIGS. 1 and 2, the side pulls are sewn to the compression pad. However, the invention is not restricted to this means of affixation, but also includes arrangements wherein the side pulls may be detachably secured to the compression pad, as by hook and loop or equivalent securement. The side pulls are formed in the conventional manner with outer and inner pieces 30 and 32. The distal ends of both side pulls are provided with hooks 34 and 36 on their inner surfaces, and the side pull 26 has loops 38 on its distal outer surface.

The method of wearing the back support belt is as follows: the lumbar belt is put on a wearer by wrapping the belt flaps around the waistline and securing the belt flaps to one another in an overlying relationship. The hook and loop material on the flaps provides the attachment of one flap to the other. The inner side pull 26 is then loosely secured via its hook surface 36 to loop material 22 on the outer surface of the flap 16. The outer side pull 28 is then secured to the loop material 21 on the outer surface of the other lumbar belt flap 14. The next step is to firmly secure the side pulls of the abdominal belt 12 to the loop material on the outer surface of the lumbar belt and overlappingly to itself.

Another feature of the invention is that the side pulls 26 and 28 are held in close proximity to the support belt when they are not secured to the belt. To this end the outside of the lumbar support belt has mounted thereon a pair of vertical strips of nylon strips or webbing shown at 40 and 42 in FIG. 2. These vertical strips on the outside of the support belt are located beside the inner edges of the loop material 21 and 22 on the outside of the belt. The strips 40 and 42 are positioned between the stays 20 and the loop material 21 and 22. The strips are affixed to opposite upper and lower edges 44 and 46 of the belt as by sewing. The intermediate strip portions 48 and 50 between these securements is unattached. This provides a space through which the inner pieces 32 of the side pulls pass. When the ends of the side pulls are not affixed, the vertical nylon strips hold the side pulls close to the support base or belt.

Referring to FIG. 2, quick lock release buckles 52 and 54 are attached to the outer surface of the lumbar belt at its upper edge 44. This attachment may be a nylon strip sewn to the belt. As shown in FIG. 2, the nylon strip securing the buckles may be sewn to the belt just above the upper edge of the unattached section of the vertical strips 40 and 42.

The quick lock release buckles used in the combination of the invention are readily available. Such buckles are typically made of a synthetic material and have separable male and female halves. The two halves are capable of quick positive locking into a mated relationship, and quick release from that relationship. When the two halves are brought together, locking is automatic and positive. Upon applying pressure to a movable release member, there is immediate release of the positive lock and parting of the two buckle halves. The releases may be of a center or side type. Each buckle half is adapted to be fastened to a narrow flexible strip or tape and to that end is provided with so called pass through fastening elements. These pass throughs are of a single and double type. The double pass through is adapted to providing an adjustable securement.

FIG. 2A shows the details of a typical quick lock release buckle 54 shown on the right in FIG. 2 in an unengaged positioned. The nylon strip 56 is passed through the single pass through 58 at one edge of the female half 60 of the buckle. The male half 62 of the buckle is provided with a two pass securement 64.

Referring to FIG. 4, there is shown a typical apron or panel member 66 having a neck loop 68. The apron is provided with a pair of bottom pockets 70 and 72. The apron also may be provided with the traditional upper pouch and pencil pocket which are here indicated by broken lines at 74 and 76. Waist ties or scuring extentions and 80 are attached at opposite edges of the sides of the apron. These may comprise nylon webbing of up to approximately one inch in width. The ends of the nylon webbing 78 and 80 are secured through the double pass of quick release buckles 52, 54. For example in FIG. 4A, nylon webbing 80 is secured to securement 82 of the male end 84 of the quick lock release buckles. The female portions 86 of the quick lock release buckles have single feed through securement 88, and are fastened to the back of the lumbar belt by nylon stripping as previously described. The apron is mounted on the wearer by locking the buckle halves together. The double pass throughs on the waist ties provide for adjustability of fit. The use of the quick lock release buckles in this fashion permits the wearer to quickly put the apron on and take it off, while simultaneously providing adjustability of fit.

FIG. 3 shows the back support in a closed condition as it would appear when worn by a user. The quick lock release buckles 52 and 54 are seen extending from the sides of the belt. FIG. 3A shows an exploded enlarged view of the buckle 54 and shows the end of the strip 56 which is sewn to the outer side of the lumbar belt at the position of the vertical strip 42 in FIG. 2.

While the foregoing has described what are considered to be preferred embodiments of the invention, it is understood that various modifications may be made therein and that the invention may be implemented in various forms and embodiments, and that it may be applied in numerous applications, only some of which have been described herein. It is intended by the following claims to claim all such modifications and variations which fall within the true scope of the invention.

What is claimed is:

1. A back support assembly comprising:

a support belt having a back portion with flap members extending therefrom, said flap members having securable fasteners for overlappingly securing ends of said flap members to each other, side pulls having securable fasteners at outer ends extending from said back portion for overlying said flap members when said flap members are secured to each other and for overlying one another when said side pulls are secured;

each of said side pulls comprising a pair of elongated and at least partially overlying elements;

a substantially vertical strip mounted on outer surfaces of each of said flap members and fastened to said flap member substantially at upper and lower edges, each of said vertical strips being substantially unfastened between said upper and lower edges, said vertical strip of each of said flap members passing between said overlying elements of one of said side pulls to hold said side pulls to said flap members, a pair of quick release buckles spaced from each other, each quick release buckle extending substantially horizontally from one of said vertical strips and including male and female halves;

a panel member with opposing securing extensions, each securing extension adjustably secured to one of said pair of quick release buckles, wherein said securing extensions allow for adjustments with said buckles while said side pulls and flap members are secured to each other.

2. A back support assembly according to claim 1 wherein said quick release buckles have a center release.

3. A back support assembly according to claim 1 wherein said quick release buckles have a side release.

4. A back support assembly according to claim 1 wherein said panel member is an apron and said securing extensions comprise waist ties attached to said apron.

5. A back support assembly according to claim 4 wherein said waist ties are attached to said quick release buckles through a two pass securement to provide adjustability.

6. A back support assembly according to claim 1 wherein each of said quick release buckles is fastened to said vertical strip and said flap member substantially adjacent said upper edge of said flap member above said overlying elements of said side pulls.

7. A method of using the back support assembly of claim 1 comprising;

providing the back support assembly of claim 1;

positioning the support belt on the user with said quick release buckles in a released condition and said male and female halves disengaged wherein one of said male and female halves of each buckle is attached to said support belt and the other of said male and female halves of each buckle is attached to one of said securing extensions on said panel member, engaging said male and female halves of said quick release buckles to fasten said securing extensions and attached panel member to said support belt, and adjusting the attachment of said securing extensions to said other of said male and female halves of each quick release buckle to adjust the effective length of said securing extensions and thereby secure a desired fit for said panel member on the user.

\* \* \* \* \*